United States Patent
Doosa et al.

(10) Patent No.: US 11,873,276 B2
(45) Date of Patent: Jan. 16, 2024

(54) FLUIDIZED BED DEHYDROGENATION PROCESS FOR LIGHT OLEFIN PRODUCTION

(71) Applicant: Indian Oil Corporation Limited, Mumbai (IN)

(72) Inventors: Hima Bindu Doosa, Faridabad (IN); Saravanan Subramani, Faridabad (IN); Ram Mohan Thakur, Faridabad (IN); Vineeth Venu Nath, Faridabad (IN); Kumaresan Loganathan, Faridabad (IN); Bineesh Kanattukara Vijayan, Faridabad (IN); Madhusudan Sau, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/447,828

(22) Filed: Sep. 16, 2021

(65) Prior Publication Data
US 2022/0081373 A1 Mar. 17, 2022

(30) Foreign Application Priority Data
Sep. 16, 2020 (IN) .............................. 202021040124

(51) Int. Cl.
*C07C 5/333* (2006.01)
*B01J 8/24* (2006.01)
(Continued)

(52) U.S. Cl.
CPC ............. *C07C 5/333* (2013.01); *B01J 8/0055* (2013.01); *B01J 8/1836* (2013.01); *B01J 8/24* (2013.01); *B01J 38/02* (2013.01); *B01J 38/06* (2013.01); *B01J 2208/00115* (2013.01); *B01J 2208/00407* (2013.01); *B01J 2208/00557* (2013.01)

(58) Field of Classification Search
None
See application file for complete search history.

(56) References Cited

U.S. PATENT DOCUMENTS 2,412,025 A * 12/1946 Zimmerman .......... B01J 8/1836
422/223
2,727,930 A * 12/1955 Johnson .................. B01J 8/388
55/474

(Continued)

FOREIGN PATENT DOCUMENTS

WO       1995023123 A1     8/1995

*Primary Examiner* — Renee Robinson
(74) *Attorney, Agent, or Firm* — Workman Nydegger

(57) ABSTRACT

The present invention discloses process and apparatus for the production of light olefins from their respective alkanes by catalytic dehydrogenation, where in the dehydrogenation reaction is carried out in multiple semi-continuously operated fluidized bed isothermal reactors, connected to a common regenerator and wherein the process is carried out in a sequence of steps in each cycle i.e., entry of hot regenerated catalyst, pre-treatment with reducing gas, dehydrogenation reaction, stripping, transfer of catalyst to regenerator and catalyst regeneration. Process cycle in each reactor starts at different times such that the catalyst inventory in the regenerator is invariable with time.

18 Claims, 1 Drawing Sheet

(51) Int. Cl.
   *B01J 8/00*  (2006.01)
   *B01J 8/18*  (2006.01)
   *B01J 38/02* (2006.01)
   *B01J 38/06* (2006.01)

(56) References Cited

U.S. PATENT DOCUMENTS

| | | | |
|---|---|---|---|
| 5,227,566 | A | 7/1993 | Cottrell et al. |
| 7,235,706 | B2 | 6/2007 | Iezzi et al. |
| 2008/0161624 | A1* | 7/2008 | Glover ............... C07C 5/325 585/634 |
| 2010/0331589 | A1 | 12/2010 | Zimmermann et al. |
| 2012/0108877 | A1* | 5/2012 | Myers ............... C07C 5/333 585/654 |
| 2013/0158327 | A1* | 6/2013 | Leonard ............ C07C 5/333 585/654 |
| 2016/0068454 | A1* | 3/2016 | Nawaz ............. C07C 5/3337 585/654 |
| 2017/0275219 | A1* | 9/2017 | Nawaz ............. C07C 5/3337 |
| 2018/0079700 | A1* | 3/2018 | Pretz ................... B01J 8/26 |

* cited by examiner

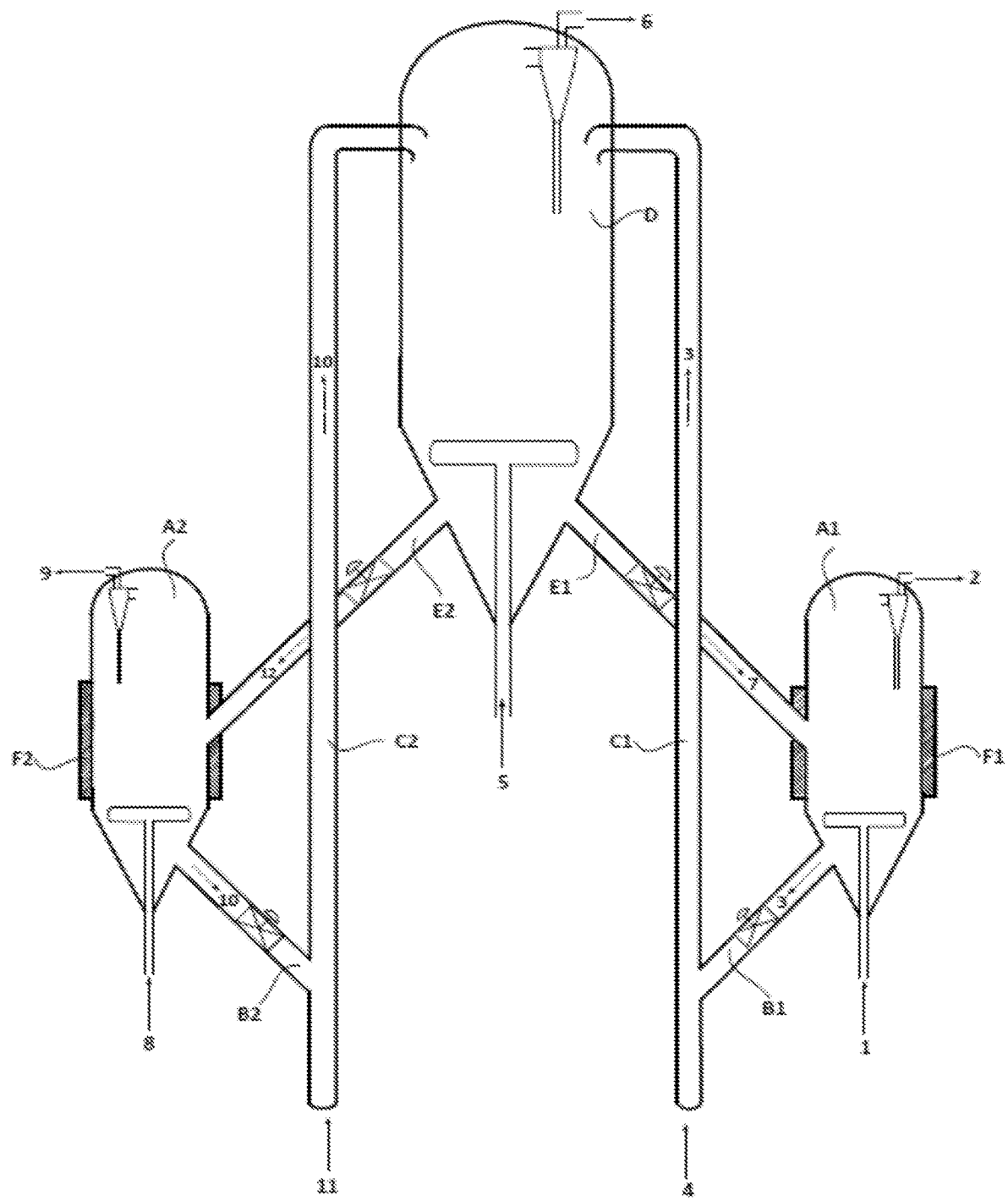

FLUIDIZED BED DEHYDROGENATION PROCESS FOR LIGHT OLEFIN PRODUCTION

FIELD OF THE INVENTION

The invention relates to production of light olefins from alkanes, particularly production of propylene from propane by catalytic dehydrogenation. Specifically, the invention discloses the process and apparatus for dehydrogenation of alkanes to light olefins.

BACKGROUND OF THE INVENTION

Light olefins, such as, ethylene, propylene and butylenes are widely used as pre-cursors or intermediates in petrochemical industry. Among these olefins, propylene is significant due to its rising global demand. Propylene is majorly obtained as by-product of steam cracking and fluid catalytic cracking (FCC) processes. In order to bridge the gap between the supply and demand of propylene, on-purpose propylene production has become essential. Propane dehydrogenation (PDH) is one such extensively adopted on-purpose propylene production process due to its simple reaction chemistry and relatively high propylene yields.

Several process technologies on catalytic dehydrogenation (DH) of alkanes to light olefins are available. WO1995023123A1 discloses an endothermic catalytic dehydrogenation process, wherein the dehydrogenation reaction occurs on fixed bed of catalyst, followed by passing a heating gas to supply heat required for endothermic DH reaction and to regenerate the catalyst by burning the coke. Catalytic dehydrogenation can be carried out in a fixed bed tubular or tube bundle reactors enclosed in a furnace. Such fixed bed systems require higher catalyst inventory resulting in large equipment size and frequent cycling of the system can lead to operational and maintenance problems.

Other processes as described in U.S. Pat. No. 7,235,706B2 comprise of fluidized bed reactor-regenerator system, where in the gas and the solids move counter-currently in both reactor and regenerator. The heat requirement for the reaction is met by burning the coke on the catalyst using air or mixture of air and fuel gas. As disclosed in U.S. Pat. No. 5,227,566A and US20100331589A1 radial moving bed reactors connected in series with intermediate heaters are also used for PDH. A continuous catalyst regenerator is employed to reactivate the catalyst by burning the coke using air and dispersing the active components of the catalyst using chlorine/chlorine-containing compound.

The drawbacks of the above prior art processes are usage of expensive noble metal containing catalyst, possible embrittlement of stainless steel reactors by chlorine, and requirement of inter-heaters. The use of several fuel fired charge heaters provides additional heat to the dehydrogenation reactors, however, results in loss of propylene yield due to undesired cracking in the heater and the associated heater transfer lines. Other problems such as fouling or coking of the charge heaters can enhance the maintenance costs.

The present invention discloses process for dehydrogenation of alkanes to light olefins which employs fixed fluidized bed reactor system, wherein the reactor operates semi-continuously and the regenerator operates continuously with no requirement of intermittent heaters or large size reactors.

SUMMARY OF THE PRESENT INVENTION

The present invention discloses process and apparatus for the production of light olefins from their respective alkanes by catalytic dehydrogenation, where in the dehydrogenation reaction is carried out in multiple semi-continuously operated fluidized bed isothermal reactors, connected to a common regenerator.

In a preferred aspect of the present invention, the process for production of light olefins by dehydrogenation of alkanes in a plurality of semi-continuously operated fluidized bed reactors ($A_i$; i=1, 2, ... n) provided with a common catalyst regenerator (D), wherein each process cycle comprises sequential steps of:
a) feeding hot regenerated catalyst and pre-heated diluent stream to fluidized bed reactors ($A_i$);
b) pretreatment of regenerated catalyst by feeding reducing gas to fluidized bed reactors;
c) feeding a pre-heated alkane feed to fluidized bed reactors for catalytic dehydrogenation in presence of pre-treated catalyst and to obtain a product mixture comprising of olefins, unreacted alkanes and other gases;
d) separating the product mixture from catalyst in the reactor cyclones;
e) separating the remaining hydrocarbons molecules from the spent catalyst by stripping using steam or nitrogen or any other inert gas and recovering the stripping product gas through reactor cyclones;
f) transferring the spent catalyst to regenerator (D); and,
g) reactivating the spent catalyst in the regenerator by burning the coke deposited on spent catalyst using air or oxygen or oxygen containing gas.

In another aspect of the present invention, the fluidized bed reactors in said process are maintained under isothermal conditions by an additional heating element ($F_i$).

In another aspect of the present invention, the process cycle in each reactor ($A_i$) begins at a different time such that the catalyst inventory in the regenerator is nearly constant with time.

In another aspect of the present invention, the dehydrogenation reaction is carried out at a temperature in the range of 500-850° C., preferably 550-700° C.; pressure in the range of 0.1-3.0 bar; and gas hourly space velocity (GHSV) of the feed stream (1) in the range of 500-10000 $h^{-1}$, and molar ratio of diluent to hydrocarbon in the feed stream is in the range of 0.1 to 5.

In another aspect of the present invention, the fluidized bed reactors have a catalyst bed density of 500-700 $kg/m^3$ in lower portion and density of 20-100 $kg/m^3$ in the upper portion, molar ratio of diluent to hydrocarbon in the feed stream is in the range of 0 to 5 and the contact time of the reaction mixture and the catalyst in fluidized bed reactors is 0.1-20 seconds, preferably 0.5-10 seconds.

In another aspect of the present invention, the contact time of the reaction mixture and the catalyst in fluidized bed reactors is 0.1-20 seconds, preferably 0.5-10 seconds, and the alkane conversion per pass is 40-60 wt % with olefin selectivity of 80-97 wt %.

In another aspect of the present invention, catalyst comprises of metal or metal oxides, selected from groups, IA, VB, VIB, VIII, Lanthanide series, or combination thereof; and supported on alumina, silica, zeolite, or combination thereof.

In another aspect of the present invention, the temperature of hot regenerated catalyst entering the reactor is 600-800° C., and wherein diluent stream comprises of nitrogen or steam or helium or any other gas, and wherein pre-heated alkane is sent to a reactor with or without diluents, and the average residence time of the catalyst in the regenerator is 1-10 minutes.

In another aspect of the present invention, the alkane feed stream comprises of ethane or propane or iso-butane or n-butane or any combination, and the alkane feed stream consists of alkanes, diluent, and an oxidizing agent, such as, carbon dioxide, oxygen, etc.

In another aspect of the present invention, the alkane feed stream is pre-heated to 400-700° C. in an external furnace prior to sending to the reactor, and the reducing gas is selected from the group consisting of hydrogen or methane or hydrogen containing gas or dry gas from FCCU or Pressure Swing Adsorption (PSA) off-gas from Hydrogen Generation Unit (HGU) or any combination thereof, and wherein the heat produced by burning the coke deposited on catalyst is utilized in the reactor.

In a preferred aspect, pretreatment of catalyst (reduction) enhances the propylene selectivity by regulating the oxidation states of the active metals in the catalyst.

In another aspect of the present invention, the temperature of the catalyst in regenerator is 600-800° C., the average residence time of the catalyst in the regenerator is 1-10 minutes, and wherein the heat produced by burning the coke deposited on catalyst is utilized in the reactor.

In another aspect of the present invention, during reactivation of spent catalyst from reactor Ai, minimum catalyst inventory is maintained in reactor $A_i$, using steam or nitrogen or any inert gas flowing at minimum velocity, and wherein to compensate the catalyst losses from inventory and to maintain uniform catalyst activity, small amount of fresh catalyst is added and/or small amount of spent catalyst is withdrawn at regular intervals of time.

In another aspect of the present invention the alkane feed stream comprises of ethane or propane or iso-butane or n-butane or any combination.

In another preferred aspect, the number of reactors (n) is a function of time taken for completion of one process cycle or cycle time ($t_C$), time taken for catalyst regeneration ($t_{Rg}$), and time taken for transfer of catalyst from reactor to regenerator or time taken for transfer of catalyst from regenerator to reactor ($t_T$).

In another preferred aspect, the number of reactors is directly proportional to the cycle time, and inversely proportional to the time taken for catalyst regeneration and catalyst transfer.

In another preferred aspect, ethane, propane, iso-butane, or n-butane are sent to separate reactors for simultaneous production of ethylene, propylene and butylenes, respectively.

In a preferred aspect, an apparatus for production of light olefins by dehydrogenation of alkanes comprising:
  a) plurality of fluidized bed reactors ($A_i$) comprising of gas distributors, and set of cyclones,
  b) a regenerator (D),
  c) vertical lift line ($C_i$),
  d) standpipes ($B_i$) to transfer spent catalyst to respective lift lines ($C_i$),
  e) standpipes ($E_i$) to transfer regenerated catalyst to respective reactors ($A_i$) and
  f) optionally heating elements ($F_i$),
wherein bottom section of the reactor $A_i$ is connected to the lower section of vertical lift line $C_i$ through standpipe $B_i$, respectively;
wherein bottom section of the regenerator D is connected to the reactors $A_i$ through standpipes $E_i$, respectively;
wherein top section of the lift lines $C_i$ terminate in the regenerator D.

In another preferred aspect, the number of fluidized bed reactors is proportional to the process cycle.

In another aspect of the present invention, the fluidized bed reactors ($A_i$) comprising of a gas distributor for introducing feed mixture or diluents or reducing gas; a set of cyclones for separation of catalyst and product mixture; and the fluidized bed reactors ($A_i$) is adapted to accommodate a pre-heated alkane feed stream (1) and a catalyst for dehydrogenation reaction.

In another aspect of the present invention, the regenerator (D) comprises a gas distributor at the bottom for supplying air or oxygen or oxygen containing gas, and a set of cyclones for separation of catalyst from flue gas.

In another aspect of the present invention the standpipes ($B_i$, $E_i$) comprise of slide valves to regulate the catalyst flow.

In another aspect of the present invention, sequence of steps in each reactor are, entry of hot regenerated catalyst, pre-treatment with reducing gas, dehydrogenation reaction, stripping, transfer of catalyst to regenerator. The reaction step in each reactor starts at different times such that the catalyst inventory in the regenerator is invariable with time. Longer cycle time in the isothermal reactors enhances the catalyst life.

In another aspect of the present invention, heating element ($F_i$) is an electrical furnace surrounding the reactor or a heating surface inserted into the dense bed of the reactor or any other known form of heating without direct exposure to the catalyst.

In another aspect of the present invention, simultaneous dehydrogenation of alkanes with carbon number 2 to 5 can be carried out in different reactors.

BRIEF DESCRIPTION OF THE DRAWINGS

FIGURE: illustrates a schematic view of an apparatus for dehydrogenation of alkanes, according to an embodiment of the present disclosure.

OBJECTIVES OF THE PRESENT INVENTION

It is a primary objective of the invention which relates to a process for the production of light olefins.

It is the further objective of the present invention relates to an apparatus for the production of light olefins.

Another objective of the disclosed invention is to improve the catalyst life by increasing the reaction cycle time.

Another objective of the disclosed invention is to carry out dehydrogenation of ethane, propane, and iso-butane simultaneously.

DESCRIPTION OF THE INVENTION

According to the main embodiment, the present invention discloses a process for the production of light olefins from alkanes by catalytic dehydrogenation. The aforesaid process employs several isothermally operated fluidized bed reactors connected to a common fluidized bed regenerator.

In another embodiment of the present invention, each reactor operates in semi-continuous mode with the sequence of steps as, transfer of hot regenerated catalyst to reactor, catalyst pre-treatment using reducing gas, dehydrogenation reaction, stripping and transfer of spent catalyst to regenerator. When reaction occurs in one reactor, pre-treatment or reaction or stripping or catalyst transfer occurs in the other reactors and thus the starting time of process cycle is different in different reactors. The number of reactors in the aforesaid process depends on the process cycle time such that the catalyst inventory in the regenerator is nearly constant with time. After the reaction and stripping step in the reactor, the catalyst is transferred to regenerator through a vertical lift line. The coke deposited on the catalyst is combusted using air or oxygen or oxygen containing gas or combination thereof. The regenerated catalyst is transferred back to the reactor through a standpipe in such a way that a seal of catalyst or slide valve always exists between reactor and regenerator. The flow of catalyst in the stand pipes is regulated by slide valves.

Since the alkane dehydrogenation reaction is highly endothermic, the reactor temperature drops as the reaction proceeds. This results in drastic decrease of alkane conversion and reaction step has to be terminated at this point to maintain steady product yield pattern. In the present invention, continuous external heat is supplied to the reactor to maintain the reaction temperature nearly constant and thus providing steady alkane conversion and product yields for longer duration. The reaction step ends when the alkane conversion falls below the desired value due to the deposition of coke on the catalyst. Thus, the cycle time is enhanced resulting in ease of operation. The heat produced by burning the coke is utilized for subsequent process steps in the reactor, and thus, additional fuel is not required to be added in the regenerator. When fuel is combusted in the regenerator, the catalyst not only gets heated up but also has possibility of sintering at high temperatures. Additional heat by burning of fuel or from other sources may be required during start-up of the plant. Thus, the disclosed invention has additional advantage of enhanced catalyst life and ease of operation. Further, the dehydrogenation of ethane, propane and butane/iso-butane can be performed simultaneously in different reactors. The process of the present invention is exemplified by, but not limited to the following figures and examples.

In another embodiment of the present invention, the schematic diagram of the fluidized bed reactor system for dehydrogenation of light alkanes to their respective olefins is represented in FIGURE. The apparatus comprises plurality of fluidized bed reactors ($A_i$; where i=1, 2, 3, . . . n) comprising of gas distributor at the bottom for introducing feed mixture or diluents or reducing gas and a set of cyclones for separation of product gases from the catalyst. The bottom section of the reactor $A_i$ is connected to the lower section of vertical lift line Ci through standpipe $B_i$. The top section of the lift line $C_i$ is terminated in the regenerator D. The bottom section of the regenerator D is connected to the respective reactors $A_i$ (i=1, 2, 3, . . . n) through standpipes Ei. For isothermal operation, an additional heating element $F_i$ is provided. The heating element can be an electrical furnace surrounding the reactor or a heating surface inserted into the dense bed of the reactor or any other known form of heating without direct exposure to the catalyst.

In another preferred embodiment of the present invention, process for production of light olefins illustrated by FIGURE, the slide valve of the stand pipe $E_i$ opens (t=0 mins) and the hot regenerated catalyst (7) at temperature of 600-800° C. flows into the reactor $A_i$ until the desired catalyst inventory is built up. The slide valve of stand pipe $B_i$ remains closed at this condition. The pre-heated diluent stream comprising of nitrogen or steam or Helium or any other inert gas, flows continuously upwards from the gas distributor of reactor $A_i$ during catalyst loading, and the diluent flow rate is gradually increased with the amount of catalyst loaded. Once the slide valve of the stand pipe $E_i$ closes, the diluent flow is reduced or stopped and the reducing gas is supplied to the reactor through the gas distributor. The reducing gas is hydrogen or methane or hydrogen containing gas or dry gas from fluid catalytic cracking unit (FCCU) or Pressure Swing Adsorption (PSA) off-gas from Hydrogen Generation Unit (HGU) or any combination thereof. Treatment of catalyst with reducing gas prior to reaction not only enhances the propylene selectivity by regulating the oxidation states of the active metals on the catalysts, but also provides additional heat for the reaction. Supporting data showing the effect of pre-treatment of catalyst by reducing gas is provided as example 2.

In another embodiment of the present invention, after the pre-treatment (reduction) of catalyst, the reducing gas gets switched-off and the pre-heated alkane feed stream with or without diluents (1) enters the reactor through the gas distributor. The alkane feed stream comprising of ethane or propane or iso-butane or n-butane or any combination thereof is pre-heated to 400-700° C. in an external furnace prior to sending to the reactor. The reactor comprises of catalyst in fluidized bed condition with lower portion of bed having a density of 500-700 kg/m$^3$ and upper part having a density of 20-100 kg/m$^3$. The reactor is fluidized to conditions that uniform temperature is maintained in the reactor and proper mixing of catalyst and feed is ensured. The mixture of pre-heated feed and diluents comes in contact with the dehydrogenation catalyst in the reactor, wherein the alkanes are dehydrogenated to respective olefins. The product mixture comprising of olefins, unreacted alkanes, and other gases (2) move upward, get separated from the catalyst in reactor cyclones, and exits the reactor for further separation. The dehydrogenation reaction temperature is 500-850° C., preferably 550-700° C. Reaction pressure is 0.1-3.0 bar, gas hourly space velocity (GHSV) of the feed stream (1) is 500-10000 h$^{-1}$ and the molar ratio of diluent to hydrocarbon in the feed stream is in the range of 0.1 to 5. The contact time of the reaction mixture and the catalyst is 0.1-20 seconds, preferably 0.5-10 seconds. The alkane dehydrogenation reaction occurs continuously in the reactor till the catalyst is coked up and decline in the alkane conversion is observed, i.e., for 1-5 hours. The average alkane conversion achieved per pass is 40-60 wt % with olefin selectivity of 80-97 wt %.

Following the reaction step, the stripping step begins wherein the hydrocarbons are stripped off from the catalyst using steam or nitrogen or any other inert gas. The stripping product gas is also sent for separation/recovery through the reactor cyclones. When the catalyst stripping is completed, the slide valve of stand pipe $B_i$ opens and the spent dehydrogenation catalyst (3) flows to the lift line $C_i$, wherein the catalyst is lifted upwards into the regenerator D using steam or nitrogen or any other inert gas (4).

In the regenerator D, the spent catalyst is reactivated by burning the coke deposited on the catalyst by supplying air or oxygen or oxygen containing gas (5) from a gas distributor at the bottom of the regenerator. The flue gas (6) generated exits the regenerator D through a set of cyclones. The temperature of the catalyst in regenerator is 600-800° C. and the average residence time of the catalyst in the regenerator is 1-10 minutes. During catalyst regeneration, the reactor $A_i$ has minimum catalyst inventory with steam or nitrogen or any inert gas flowing at minimum velocity and slide valve of stand pipe $B_i$ closed. As the regeneration gets completed, the slide valve of the stand pipe $E_i$ opens and the hot regenerated catalyst (7) enters the reactor $A_i$ and next cycle begins. To compensate the catalyst losses from inventory and to maintain uniform catalyst activity, small amount of fresh catalyst is added and/or small amount of spent catalyst is withdrawn at regular intervals of time.

The sequence of operation is such that, when the slide valve of the stand pipe $E_i$ opens (t=0 mins) for transfer of regenerated catalyst from regenerator D to reactor $A_i$, the slide valve of stand pipe $B_2$ opens so that the spent catalyst from reactor $A_2$ gets transferred to regenerator D through the lift line $C_2$. After regeneration, the slide valve $E_2$ opens and the hot catalyst flows into the reactor $A_2$. At the same time, the spent catalyst from reactor $A_3$ flows into the regenerator through the slide valve $B_3$ and the lift line $C_3$, and so on.

In another embodiment, the number of reactors (n) in the disclosed process is a function of time taken for completion of one process cycle or cycle time ($t_C$), time taken for catalyst regeneration ($t_{Rg}$), and time taken for transfer of catalyst from reactor to regenerator or time taken for transfer of catalyst from regenerator to reactor ($t_T$). In particular, the number of reactors is directly proportional to the cycle time, and inversely proportional to the time taken for catalyst regeneration and catalyst transfer. Thus, the step which occurred in reactor A(i−1) at time t=x occurs in the reactor $A_i$ at time t=x+($t_{Rg}$+$t_T$), where i=1, 2, ... n.

Dehydrogenation catalysts comprising of metals or metal oxides, supported on Alumina or silica or zeolite or combination thereof, or any other fluidizable dehydrogenation catalyst is used in this process. The metals are selected from groups, IA, VB, VIB, VIII, Lanthanide series, or combination thereof (as disclosed in U.S. Ser. No. 10/947,172B2 and U.S. Ser. No. 11/000,843B2). In due course of operation, the catalyst gets permanently deactivated and needs to be replaced. The disclosed process has provision for continuous catalyst addition and withdrawal, and hence, there is no requirement of unit shutdown for catalyst replacement.

In another embodiment of the process, there is no provision for external heating in the reactors and the dehydrogenation reaction is carried out under adiabatic conditions. Since alkane dehydrogenation reaction is endothermic, the catalyst bed temperature decreases with time leading to decrease in alkane conversion. Therefore, the reaction step ends when the reactor temperature drops below desired value of conversion. The spent catalyst after stripping is transferred to the regenerator, wherein the catalyst is regenerated by combusting the coke deposited on the catalyst in the presence of air or oxygen or mixture of air and fuel.

In another embodiment, the feed stream comprises of alkanes, diluent and/or an oxidizing agent, such as, carbon dioxide, oxygen, etc.

In another embodiment, the alkane feed is different for different reactors. For example, ethane, propane, iso-butane, or n-butane are sent to separate reactors for simultaneous production of ethylene, propylene and butylenes, respectively.

Example 1

This example illustrates the performance of catalyst in fixed bed reactor system at simulated process conditions. CAT-A, having physical properties as given in table 1 is used in the process. The catalyst was subjected to reduction using $H_2$ gas at 600-750° C. prior to DH reaction. The catalyst was evaluated using a fixed-bed tubular reactor of 9 mm ID containing 1.618 g catalyst at reaction temperature in the range of 8580-650° C., as measured by the thermocouple located in the catalyst bed. The feed stream contained propane and $N_2$ in the molar ratio of $C_3:N_2$=1:2 and Gas hourly space velocity (GHSV) of the feed gas was 2750 $h^{-1}$.

TABLE 1

Physical properties of CAT-A

| S. no. | Property | Value |
|---|---|---|
| 1. | Surface area (m²/g) | 124 |
| 2. | Average bulk density (g/cc) | 0.86 |
| 3. | Pore volume (cc/g) | ~0.2 |
| 4. | Average particle size (μm) | 99.8 |

The flow rates of inlet gases were controlled by mass flow controllers. The inlet and outlet gas compositions were analyzed in a Refinery Gas Analyzer equipped with TCD and FID at regular intervals. Propane conversion, propylene yield and selectivity were calculated using the formulae given below, and the obtained results are summarized in Table 2.

$$\% \text{ Conversion} = \frac{\text{weight of propane (in)} - \text{weight of propane (out)}}{\text{weight of propane (in)}} * 100$$

$$\% \text{ Yield} = \frac{\text{weight of propylene formed}}{\text{weight of propane (in)}} * 100$$

$$\% \text{ Selectivity} = \frac{\text{Propylene yield}}{\text{Propane conversion}} * 100$$

TABLE 2

Performance of the CAT-A at simulated process conditions

| Run time (mins) | 20 | 60 | 120 |
|---|---|---|---|
| Propane conversion (wt %) | 47.9 | 46.6 | 41.2 |
| Propylene selectivity (wt %) | 88.0 | 87.7 | 87.0 |

Example 2

This example shows the effect of pretreatment of catalyst with reducing gas on the catalyst performance. CAT-A with physical properties as given in table 1 was evaluated at the process conditions given in example 1 without reduction using hydrogen. The catalyst performance (at 20 mins of run time) with and without reduction with hydrogen is compared in table 3.

TABLE 3

Comparison of performance of CAT-A with and without hydrogen reduction at simulated process conditions

| Run time (mins) | without reduction | with reduction |
|---|---|---|
| Propane conversion (wt %) | 57.3 | 47.9 |
| Propylene selectivity (wt %) | 78.5 | 88.0 |

Advantages of the Invention

Novel process and reactor configuration to produce light olefins by catalytic dehydrogenation of corresponding alkanes.
No requirement of inter-heaters or large size reactors.
Ease & flexibility in operation.
Higher yield and selectivity of olefins.

Provision for simultaneous dehydrogenation of ethane, propane, iso-butane, etc.

Continuous catalyst addition and withdrawal without unit shutdown.

Hydrogen recycle to reactor is not required.

Enhanced catalyst life due to reduced number of reaction-regeneration cycles.

Separate sections for reaction and regeneration ensure that hydrocarbons are not intermixed with oxygen/air.

Disclosed fluidized bed process operates at pressures above atmospheric pressures, and hence, no possibility of permeation of ambient air into the system.

What is claimed is:

1. A process for production of light olefins by dehydrogenation of alkanes in a plurality of semi-continuously operated fluidized bed reactors $A_i$; (i=2, ... n) provided with a common continuously operated catalyst regenerator (D), wherein the process comprises sequential steps:
   a) feeding a hot regenerated catalyst and a pre-heated diluent stream to the plurality of semi-continuously operated fluidized bed reactors;
   b) pre-treating the hot regenerated catalyst by feeding a reducing gas to the plurality of semi-continuously operated fluidized bed reactors to obtain a pre-treated catalyst;
   c) feeding a pre-heated alkane feed to the plurality of semi-continuously operated fluidized bed reactors for catalytic dehydrogenation in presence of the pre-treated catalyst to obtain a product mixture comprising olefins, unreacted alkanes, product gases, and a spent catalyst;
   d) separating the product mixture from the spent catalyst in reactor cyclones;
   e) separating remaining hydrocarbon molecules from the spent catalyst by stripping using steam, or an inert gas and recovering stripping product gas through the reactor cyclones;
   f) transferring the spent catalyst to the common continuously operated catalyst regenerator (D); and,
   g) reactivating the spent catalyst in the common continuously operated catalyst regenerator by burning coke deposited on spent catalyst using air, oxygen, or an oxygen containing gas, wherein the pre-heated diluent stream and the pre-heated alkane feed are in a molar ratio in a range of 0.1 to 5, wherein the process in each of the plurality of semi-continuously operated fluidized bed reactors begins at a different time to maintain a constant catalyst inventory with time in the common continuously operated catalyst regenerator, and to maintain a minimum catalyst inventory in each of the plurality of semi-continuously operated fluidized bed reactors by flowing steam, or an inert gas at a minimum velocity during reactivation of the spent catalyst, wherein the process occurs in a sequence wherein a slide valve of a stand pipe opens at t=0 minutes to transfer the regenerated catalyst from the common continuously operated catalyst regenerator to the semi-continuously operated fluidized bed reactor $A_{i-1}$, and wherein a slide valve of a stand pipe $B_{i-1}$ remains closed at t=0 minutes until a desired catalyst inventory is built up in the semi-continuously operated fluidized bed reactor $A_{i-1}$, the slide valve of the stand pipe $B_i$ opens to transfer the spent catalyst from the semi-continuously operated fluidized bed reactor $A_i$ to the common continuously operated catalyst regenerator through a lift line $C_i$, wherein after regeneration, a slide valve of a stand pipe $E_i$ opens and the hot regenerated catalyst flows into the semi-continuously operated fluidized bed reactor $A_i$, and wherein at the same time, the spent catalyst from the semi-continuously operated fluidized bed reactor $A_{i+1}$ flows into the common continuously operated catalyst regenerator through a slide valve of a stand pipe $B_{i+1}$ and the lift line $C_{i+1}$, where i=2, ... n.

2. The process as claimed in claim 1, wherein the semi-continuously operated fluidized bed reactors are maintained under isothermal conditions by an additional heating element (Ft).

3. The process as claimed in claim 1, wherein the temperature of the hot regenerated catalyst entering the plurality of semi-continuously operated fluidized bed reactors is 600-800° C., and wherein the pre-heated diluent stream comprises of nitrogen, steam, or helium, and wherein the pre-heated alkane feed is sent to the plurality of semi-continuously operated fluidized bed reactors with or without diluents.

4. The process as claimed in claim 1, wherein the reducing gas is selected from the group consisting of hydrogen, methane, a hydrogen containing gas, a dry gas from an FCCU, Pressure Swing Adsorption (PSA) off-gas from Hydrogen Generation Unit (HGU), and a combination thereof.

5. The process as claimed in claim 1, wherein the dehydrogenation reaction is carried out at a temperature in a range of 500-850° C., a pressure in a range of 0.1-3.0 bar, and wherein the hot regenerated catalyst and the pre-heated diluent stream are fed at a gas hourly space velocity (GHSV) in a range of 500-10000 $h^{-1}$.

6. The process as claimed in claim 1, wherein the alkane feed comprises ethane, propane, iso-butane, n-butane, or a combination thereof.

7. The process as claimed in claim 6, wherein ethane, propane, iso-butane, or n-butane are sent separately to each of the plurality of the semi-continuously operated fluidized bed reactors for simultaneous production of ethylene, propylene and butylene, respectively.

8. The process as claimed in claim 1, wherein the plurality of semi-continuously operated fluidized bed reactors has a catalyst bed density of 500-700 $kg/m^3$ in a lower portion and a catalyst bed density of 20-100 $kg/m^3$ in an upper portion.

9. The process as claimed in claim 1, comprising contacting the pre-treated catalyst and the pre-heated alkane feed for a period of 0.1-20 seconds.

10. The process as claimed in claim 1, wherein 40-60 wt % of the alkane feed gets converted per pass through each of the plurality of semi-continuously operated fluidized bed reactors with an olefin selectivity of 80-97 wt %.

11. The process as claimed in claim 1, further comprising adding a fresh catalyst and withdrawing the spent catalyst at regular intervals of time to compensate the catalyst losses from the catalyst inventory and to maintain uniform catalyst activity.

12. The process as claimed in claim 1, wherein pre-treating the hot regenerated catalyst is characterized to enhance propylene selectivity.

13. The process as claimed in claim 1, wherein the number of semi-continuously operated fluidized bed reactors (n) is a function of time taken for completion of one cycle of the process ($t_C$), time taken for the spent catalyst regeneration ($t_{Rg}$), and time taken for a transfer of the spent catalyst from each of the plurality of semi-continuously operated fluidized bed reactors to the common continuously operated catalyst regenerator or time taken for a transfer of the hot regenerated catalyst from the common catalyst to each of the plurality of semi-continuously operated fluidized bed reactors ($t_T$).

14. The process as claimed in claim 1, wherein the number of semi-continuously operated fluidized bed reactors is directly proportional to the time taken for completion of one cycle of the process, and inversely proportional to the time taken for the spent catalyst regeneration and time taken for a transfer of the spent catalyst from each of the plurality of semi-continuously operated fluidized bed reactors to the common continuously operated catalyst regenerator or time taken for a transfer of the hot regenerated catalyst from the common continuously operated catalyst regenerator to each of the plurality of semi-continuously operated fluidized bed reactors.

15. The process as claimed in claim 1, wherein the alkane feed is pre-heated to 400-700° C. in an external furnace prior to sending to the plurality of semi-continuously operated fluidized bed reactors.

16. The process as claimed in claim 1, wherein the catalyst comprises metals or metal oxides selected from groups IA, VB, VIB, VIII, Lanthanide series, or a combination thereof; and is supported on alumina, silica, zeolite, or a combination thereof.

17. The process as claimed in claim 1, wherein the catalyst has a temperature in a range of 600-800° C., and an average residence time in a range of 1-10 minutes in the common continuously operated catalyst regenerator, and wherein heat produced by burning coke deposited on the catalyst is utilized in the plurality of semi-continuously operated fluidized bed reactors.

18. The process as claimed in claim 1, wherein the alkane feed consists of alkanes, diluents, and oxidizing agents, wherein the oxidizing agents comprise carbon dioxide, or oxygen.

\* \* \* \* \*